(12) United States Patent
Guo et al.

(10) Patent No.: US 12,347,547 B2
(45) Date of Patent: Jul. 1, 2025

(54) AUTOMATIC PLANNING METHOD AND DEVICE FOR TISSUE ABLATION

(71) Applicants: Shanghai Shende Green Medical Era Healthcare Technology Co., Ltd., Shanghai (CN); Shende (Ningbo) Medical Device Technology Co., Ltd, Ningbo (CN); Nantong Shende Medical Device Technology Co., Ltd, Nantong (CN)

(72) Inventors: Junjie Guo, Shanghai (CN); Shengfa Zhang, Shanghai (CN); Bo Wei, Shanghai (CN); Bo Yang, Shanghai (CN); Jiawei Gu, Shanghai (CN); Hao Wu, Shanghai (CN); Zihao Liu, Shanghai (CN); Zhiqiang Su, Shanghai (CN); Jiabao Wen, Shanghai (CN)

(73) Assignees: Shanghai Shende Green Medical Era Healthcare Technology Co., Ltd., Shanghai (CN); Shende (Ningbo) Medical Device Technology Co., Ltd, Ningbo (CN); Nantong Shende Medical Device Technology Co., Ltd, Nantong (CN)

( * ) Notice: Subject to any disclaimer, the term of this patent is extended or adjusted under 35 U.S.C. 154(b) by 94 days.

(21) Appl. No.: 18/180,372

(22) Filed: Mar. 8, 2023

(65) Prior Publication Data
US 2023/0223129 A1    Jul. 13, 2023

Related U.S. Application Data

(63) Continuation of application No. PCT/CN2021/082586, filed on Mar. 24, 2021.

(30) Foreign Application Priority Data

Sep. 9, 2020  (CN) .......................... 202010941482.6

(51) Int. Cl.
| | | |
|---|---|---|
| *G16H 20/40* | (2018.01) | |
| *A61B 34/10* | (2016.01) | |
| *G06T 19/00* | (2011.01) | |

(52) U.S. Cl.
CPC ............. *G16H 20/40* (2018.01); *A61B 34/10* (2016.02); *G06T 19/00* (2013.01);
(Continued)

(58) Field of Classification Search
CPC ............. A61B 34/00; A61B 2034/104; A61B 2034/105; G06T 19/00; G06T 2219/2008
(Continued)

(56) References Cited

U.S. PATENT DOCUMENTS

| | | | |
|---|---|---|---|
| 2002/0040220 A1 | 4/2002 | Zvuloni et al. | |
| 2009/0118613 A1* | 5/2009 | Krugman | A61B 34/10 |
| | | | 600/407 |

(Continued)

FOREIGN PATENT DOCUMENTS

| | | |
|---|---|---|
| CN | 102781356 A | 11/2012 |
| CN | 105534593 A | 5/2016 |

(Continued)

OTHER PUBLICATIONS

Porter, Brian Christopher; Three-dimensional medical ultrasound acquisition and data registration and fusion; University of Rochester. ProQuest Dissertations & Theses, 2005. 3169589. (Year: 2005).*

(Continued)

*Primary Examiner* — Hiep V Nguyen
(74) *Attorney, Agent, or Firm* — Westbridge IP LLC

(57) ABSTRACT

Disclosed are an automatic planning method and a device for tissue ablation. The method includes: obtaining a three dimensional (3D) model of a to-be-ablated tissue through a 3D reconstruction technique; marking a cylindrical ablation point on the 3D model through an ablation planning, an axial (Continued)

direction of the ablation point is the same as a radio frequency direction of thermal ablation; and displaying an ablated area on the 3D model, the reconstruction technique includes: obtaining slice images of the to-be-ablated tissue in a plurality of directions, the slice image in each direction includes a plurality of two dimensional (2D) images; depicting, by a primitive, the to-be-ablated tissue on the 2D images in one direction; and constructing the 3D model of the to-be-ablated tissue through the 3D reconstruction technique based on the original 2D images.

8 Claims, 7 Drawing Sheets

(52) U.S. Cl.
CPC ... *A61B 2034/104* (2016.02); *A61B 2034/105* (2016.02); *G06T 2219/2008* (2013.01)

(58) Field of Classification Search
USPC .............................................................. 705/2
See application file for complete search history.

(56) References Cited

U.S. PATENT DOCUMENTS

| | | |
|---|---|---|
| 2012/0237105 A1 | 9/2012 | Mielekamp |
| 2014/0064449 A1 | 3/2014 | Deng et al. |
| 2017/0209220 A1 | 7/2017 | Krugman et al. |
| 2017/0224402 A1 | 8/2017 | Borsic |
| 2020/0008875 A1 | 1/2020 | Lu |
| 2020/0179051 A1 | 6/2020 | Miga et al. |

FOREIGN PATENT DOCUMENTS

| | | | | |
|---|---|---|---|---|
| CN | 107049475 A | | 8/2017 | |
| CN | 108805991 A | | 11/2018 | |
| CN | 109077804 A | | 12/2018 | |
| CN | 110458950 A | * | 11/2019 | |
| CN | 111012484 A | | 4/2020 | |
| CN | 111067618 A | | 4/2020 | |
| CN | 111429432 A | | 7/2020 | |
| CN | 112007289 A | | 12/2020 | |
| CN | 111598998 B | * | 11/2023 | ............. G06N 3/045 |
| WO | WO-2011080666 A1 | * | 7/2011 | ............. A61B 18/12 |

OTHER PUBLICATIONS

Frakes, David Harold; An adaptive control grid interpolation technique for the three-dimensional reconstruction of MRI data; Georgia Institute of Technology. ProQuest Dissertations & Theses, 2003. 3095719. (Year: 2003).*

Gibbs, Jason D.; Three dimensional route planning for medical image reporting and endoscopic guidance; The Pennsylvania State University. ProQuest Dissertations & Theses, 2008. 3336028. (Year: 2008).*

Extended European Search Report issued in counterpart Europe Patent Application No. 21865506.6, dated Aug. 5, 2024.

First Office Action issued in counterpart Chinese Application No. 202010941482.6, dated May 23, 2022.

International Search Report and Written Opinion issued in corresponding PCT Application No. PCT/CN2021/082586, dated Jun. 24, 2021.

* cited by examiner

AUTOMATIC PLANNING METHOD AND DEVICE FOR TISSUE ABLATION

CROSS-REFERENCE TO RELATED APPLICATIONS

This application is a continuation application of International Application No. PCT/CN2021/082586, filed on Mar. 24, 2021, which claims priority to Chinese Patent Application No. 202010941482.6, filed on Sep. 9, 2020. The disclosures of the above-mentioned applications are incorporated herein by reference in their entireties.

TECHNICAL FIELD

The present disclosure relates to the technical field of medical technology, in particular to an automatic planning method and a device for tissue ablation.

BACKGROUND

Ultrasonic thermotherapy treatment of tumors is gradually and widely used clinically due to its features of non-invasive treatment. During ultrasonic treatment, it is necessary to use non-invasive monitoring technologies such as magnetic resonance and B-mode ultrasonography to image the treatment position. Imaging is used for lesion identification, sensitive tissue identification, automatic planning system for ablation area, temperature monitoring during treatment, and patient movement monitoring. In the planning of traditional ultrasonic thermotherapy, two dimensional (2D) images are used as the reference images for planning, such as magnetic resonance, ultrasonic and computed tomography (CT). During planning, doctors will add corresponding planning elements to images in different directions, including lesion area, skin, energy-blocked areas, low energy density areas, important organs, blood vessels and nerves, etc. These planning elements play a vital role in safe and effective thermotherapy for patients. Therefore, during each ultrasonic thermal ablation process, it is necessary to fully consider the impact of this thermotherapy process on the patient's important organs, blood vessels and other sensitive tissues, including whether the expected thermal effect can be accurately produced at the target point, whether it will overheat the lesion tissue, and whether it will cause unexpected damage to the patient's important organs, blood vessels or sensitive tissues, etc., if necessary, it is required to calculate the data such as the distance and the direction of the heating point relative to the patient's lesion, skin, sensitive tissue and other elements, thereby an optimal heating parameter suitable for the current equipment can be calculated to achieve the optimal thermotherapy effect. However, accurate data cannot be obtained directly from 2D imaging data. If the calculated relevant data is inaccurate, it may lead to incomplete treatment and increase the potential recurrence of tumors. In the traditional method, physicians need to rescan the internal situation of the patient's body, redepict the patient's lesions, skin, sensitive tissues and mark the ablated areas. The redepicted planning elements may deviate from the previously depicted planning elements, and the ablated area cannot be well identified on the image, which greatly tests the experience and technical level of the physician. If there is a deviation, it will lead to over-ablation or no ablation of a certain tissue, resulting in incomplete treatment and tumor recurrence.

As for the irregular shape or large lesion area, doctors must plan in advance how to prevent ablation points from affecting normal tissues, how many ablation points are needed and the order of these ablation points to avoid interference. As for the complicated operation, doctors must use cylindrical ablation volumes of different sizes and orientations on planning images to fill the complete range of the three dimensional (3D) tumor volume. In the planning process, inaccurate or insufficient planning will lead to incomplete treatment and potential recurrence of the tumor. Traditional methods plan in a point-by-point manner, but will greatly lengthen the process time and make the operation difficult.

SUMMARY

The main objective of the present disclosure is to provide an automatic planning method and a device for tissue ablation in order to overcome the above-mentioned defects in the prior art, which has a higher automation, higher precision and good safety.

One objective of the present disclosure can be achieved through the following technical solutions:

an automatic planning method for tissue ablation, including:
obtaining a 3D model of a to-be-ablated tissue through a 3D reconstruction technique;
marking a cylindrical ablation point on the 3D model through an ablation planning, an axial direction of the ablation point is the same as a radio frequency direction of thermal ablation; and
displaying an ablated area on the 3D model;
the 3D reconstruction technique includes:
obtaining slice images of the to-be-ablated tissue in a plurality of directions, the slice image in each direction includes a plurality of 2D images;
depicting, by a primitive, the to-be-ablated tissue on the 2D images in one direction;
constructing the 3D model of the to-be-ablated tissue through the 3D reconstruction technique based on the original 2D images;
displaying a cross section of the 3D model of the to-be-ablated tissue on the 2D image in other un-depicted directions;
the ablation planning includes:
selecting parameters of the ablation point and an implement sequence, the parameters of the ablation point include a size, a direction, and a frequency of the ablation point;
filling the ablation point on the 3D model according to the implement sequence, the filling includes:
dividing the 3D model into a plurality of ablation layers in a direction perpendicular to the radio frequency direction of thermal ablation; dividing the ablation layers into a plurality of strip-shaped first to-be-ablated blocks in the direction of radio frequency direction of thermal ablation; in response that there is the ablated area in the first to-be-ablated block, dividing the first to-be-ablated block into a second to-be-ablated block and an ablated block, the ablated block is located in front of the ablated area in the radio frequency direction of thermal ablation; and filling the ablation points of one parameter in the first to-be-ablated block and the second to-be-ablated block, which decreases heat accumulation to the to-be-ablated issue as possible, and avoids the ablated area to reach the premium ablation effect.

In an embodiment, the parameters of the ablation point further include an overlapping rate, two adjacent ablation points are overlapped when a plurality of ablation points are provided between the first to-be-ablated block and the second to-be-ablated block;

a formula for calculating a thickness D of the ablation layer is:

$$D = d \times N$$

d is a diameter of the cylindrical ablation point, and N is the overlapping rate of the two adjacent ablation points.

In an embodiment, reobtaining a 2D image when the to-be-ablated tissue moves; comparing a previous 2D image before moving and the reobtained 2D image which are in a same direction; and transforming the 3D model and the ablated area on the 3D model together into a coordinate system of the reobtained 2D image, thus avoiding the thermal ablation differential caused by the moving of the to-be-ablated tissue, which greatly improves the efficiency and the accuracy of the ablation point planning.

In an embodiment, implementing interpolation for tissues that are missing on the 2D image after depicting the 2D image of the to-be-ablated tissue, implementing interpolation for the un-depicted 2D images according to a difference between two adjacent 2D images in the same direction, improving the accuracy of depicting the primitives, further improving the accuracy of the 3D model, thus the accuracy of the ablation point planning is high.

In an embodiment, setting a loss function before constructing the 3D model, and fine-tuning the primitive on the 2D image by the loss function, a formula of the loss function Loss is:

$$Loss = 1 - (S_1 W_1 + S_2 W_2)$$

$S_1$ is a similarity of a gray gradient and a gray mean value of edges of primitives on the two adjacent 2D images, $S_2$ is a similarity of primitives on the two adjacent 2D images, $W_1$ and $W_2$ are preset weights, fine-tuning the image until the loss function value is smaller than the preset threshold, the fine-tuning includes expansion, erosion and vertex offset, which decrease the differential between the 3D model and the actual to-be-ablated issue, and improves the accuracy of the thermal ablation.

In an embodiment, an automatic planning device is provided, including: a memory and a processor, a computer program is stored in the memory, and the computer program is invoked by the processor to execute the above methods.

Compared with the prior art, the present disclosure has the following beneficial effects.

(1) The present disclosure depicts primitives on a plane image in a direction of a to-be-ablated tissue, obtains a 3D model through 3D reconstruction technique, and displays the ablated area on the 3D model simultaneously, thus avoiding excessive ablation of the tissue after multiple times of thermal ablation, and is of good safety. By providing ablation points and application sequences with a plurality of parameters, the 3D model is divided into ablation layers, and then the ablation layer is divided into long strips of the first to-be-ablated block, if an ablated area is in the first to-be-ablated blocks, dividing the first to-be-ablated block into a second to-be-ablated block and an ablated block; and filling the ablation points of one parameter in the first to-be-ablated block and the second to-be-ablated block in the radio frequency direction of thermal ablation, so that the ablation points cover the to-be-ablated tissue to the greatest extent, with high automation and high precision.

(2) The present disclosure allows two adjacent ablation points to partially overlap when filling the ablation point, to avoid no ablation and improve the accuracy of planning ablation point.

(3) The present disclosure reobtains a 2D image when the to-be-ablated tissue moves, and compares a previous 2D image before moving and the reobtained 2D image which are in a same direction, transforms the 3D model and the ablated area on the 3D model together into a coordinate system of the reobtained 2D image, to avoid the error of thermal ablation caused by the movement of the ablated tissue, and improve the efficiency and accuracy.

(4) The present disclosure complements the un-depicted 2D images according to a difference between two adjacent 2D images in the same direction, and complements tissues that are missing on the 2D image after depicting the 2D image of the to-be-ablated tissue, to improve the accuracy of depicting primitives, to further improve the accuracy of the 3D model and the accuracy of planning ablation points.

(5) Before constructing the 3D model, the present disclosure establishes a loss function based on the similarity of the primitives on two adjacent 2D images and the similarity of a gray gradient and a gray mean value of edges of primitives on the two adjacent 2D images. The image fine-tuning includes expansion, erosion and vertex offset. The error between the 3D model and the actual to-be-ablated tissue is reduced, to improve the accuracy of thermal ablation.

DETAILED DESCRIPTION OF THE EMBODIMENTS

The technical solutions of the embodiments of the present disclosure will be described in more detail below with reference to the accompanying drawings. It is obvious that the embodiments to be described are only some rather than all of the embodiments of the present disclosure. All other embodiments obtained by those skilled in the art based on the embodiments of the present disclosure without creative efforts shall fall within the scope of the present disclosure.

First Embodiment

Figure 1:
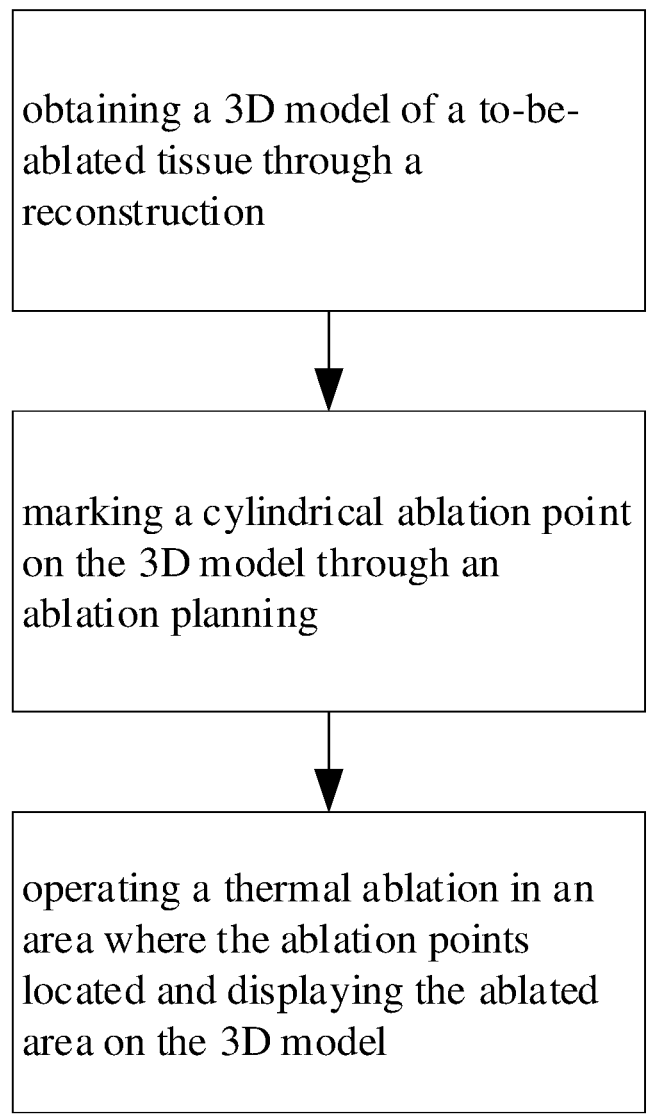
FIG. 1 is a method flowchart of the present disclosure.
Figure 2:
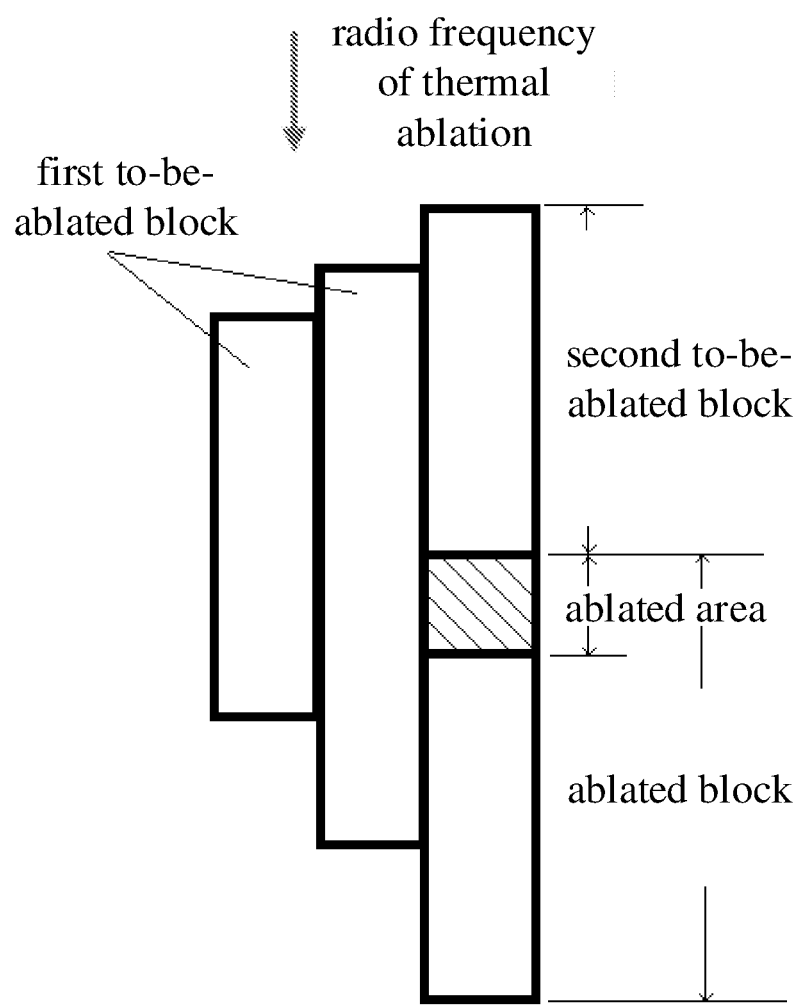
FIG. 2 is a plan view of an ablation layer before filling an ablation point.
Figure 3:
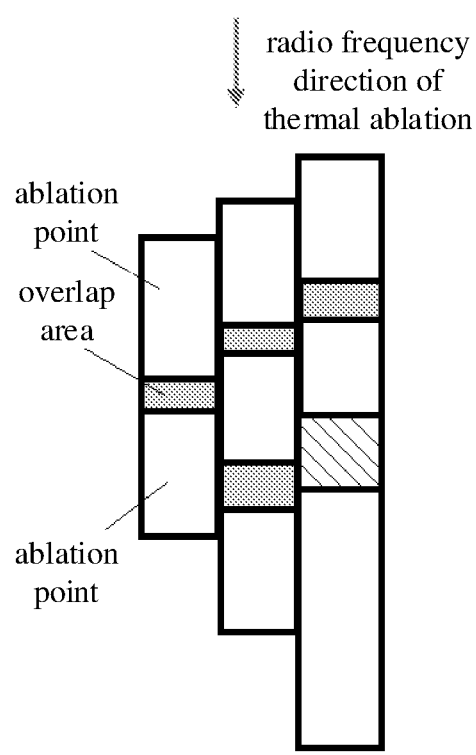
FIG. 3 is a plan view of the ablation layer after filling the ablation point.
Figure 4:
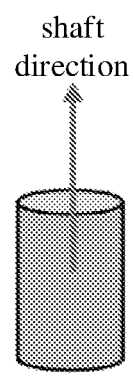
FIG. 4 is a perspective view of the ablation point.
Figure 5:
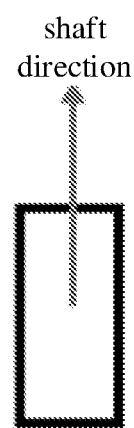
FIG. 5 is a front view of the ablation point.

An automatic planning method for tissue ablation, as shown in FIG. 1, FIG. 4 and FIG. 5, includes:

obtaining a 3D model of a to-be-ablated tissue through a 3D reconstruction technique, the to-be-ablated tissue includes lesion, skin and visceral organ; marking a cylindrical ablation point on the 3D model through an ablation planning, an axial direction of the ablation point is the same as a radio frequency direction of thermal ablation; and displaying an ablated area on the 3D model.

Figure 6:
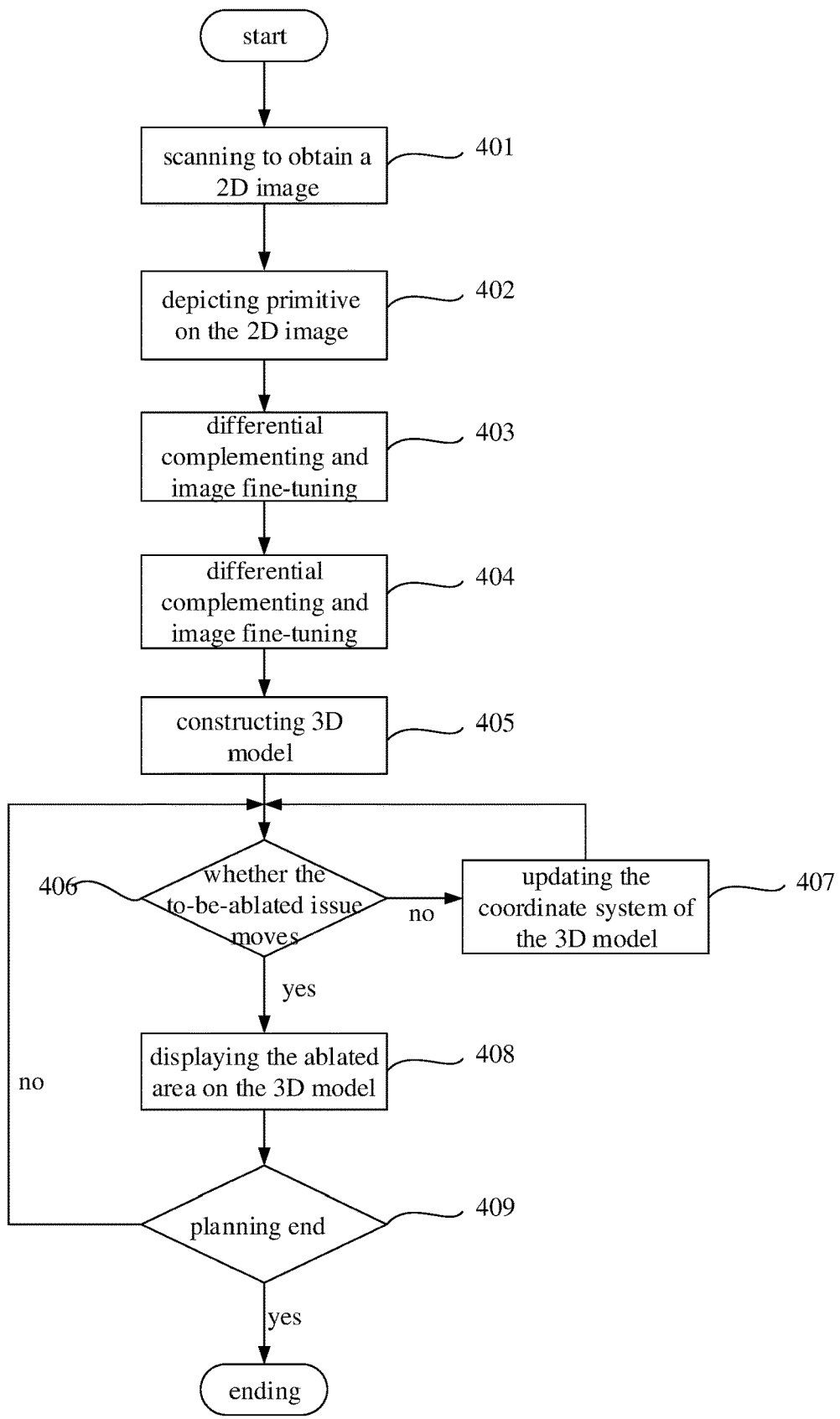
FIG. 6 is a method flowchart of 3D reconstruction technique.

As shown in FIG. 6, the 3D reconstructions technique include:

401, obtaining slice images of the to-be-ablated tissue in a plurality of directions, the slice image in each direction comprises a plurality of 2D images;

402, depicting, by a primitive, the to-be-ablated tissue on the 2D images in one of the plurality of directions by primitive including closed polygons and polylines;

403, implementing interpolation for the missing tissue on the depicted 2D images, implementing interpolation for the un-depicted 2D images based on the adjacent 2D image in the same direction;

404, using the loss function to perform image fine-tuning on the primitive on the 2D image. The image fine-tuning includes expansion, erosion and vertex offset. The calculation formula Loss of the loss function is:

$$Loss=1-(S_1W_1+S_2W_2)$$

$S_1$ is the similarity between the gray gradient and the gray mean value of the primitive on two adjacent 2D images, $S_2$ is the similarity between the primitive on two adjacent 2D images, $W_1$ and $W_2$ are the preset weights;

405, constructing a 3D model of the to-be-ablated tissue through ITK registration technique based on the original 2D image, and displaying a cross section of the 3D model of the to-be-ablated tissue on the 2D image in other un-depicted directions;

406, determining whether the to-be-ablated tissue moves, if so, executing 407, otherwise executing 408;

407, reobtaining the 2D image, comparing the two 2D images in the same direction before and after the movement, transforming the 3D model and the ablated area on the 3D model into the coordinate system of the 2D image after the movement, and executing 406;

408, updating the ablated area on the 3D model;

409, determining whether the thermal ablation is complemented according to the ablated area on the 3D model, and if so, the planning is ended; otherwise, executing 406.

Figure 7:
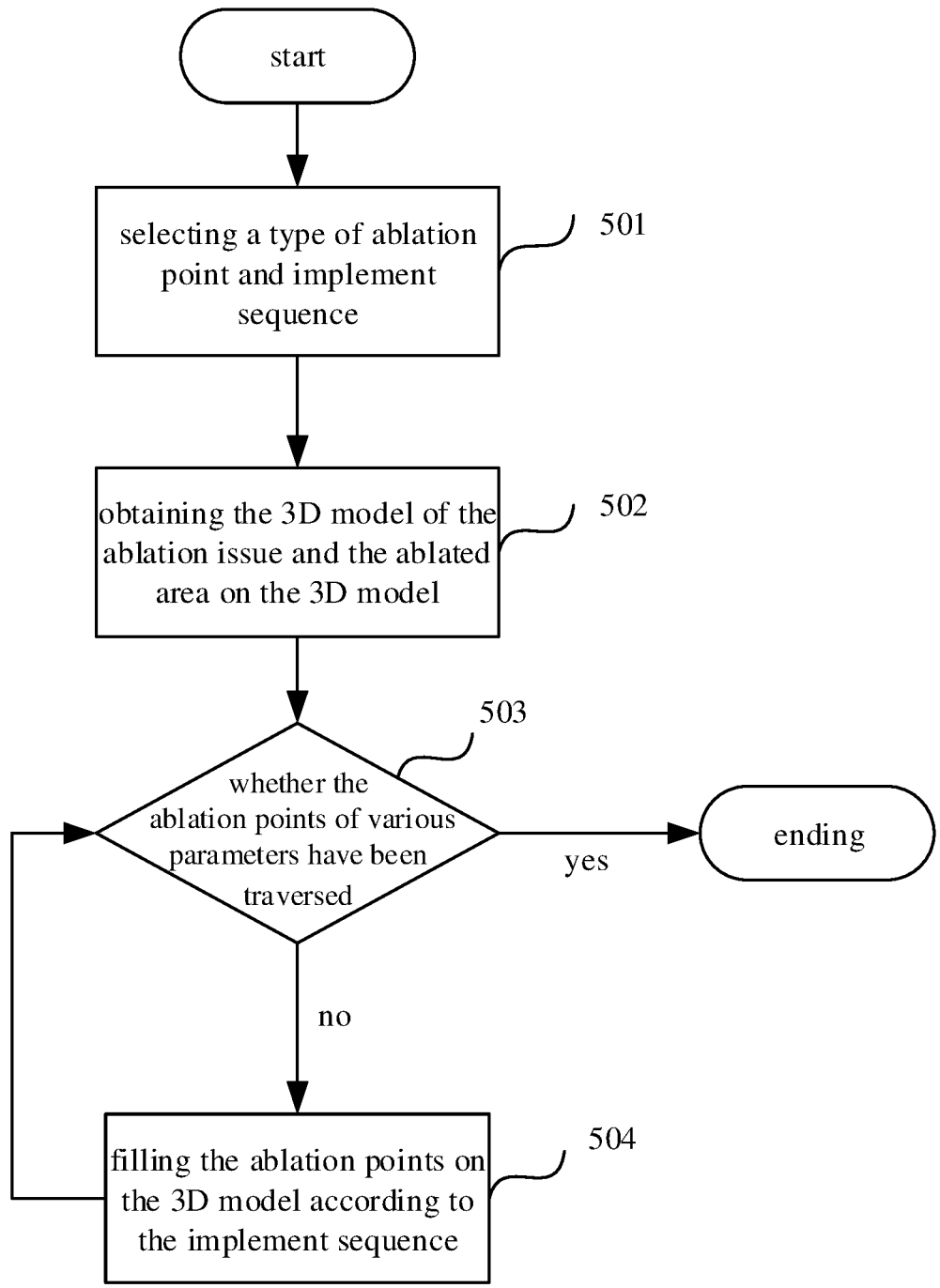
FIG. 7 is another method flowchart of the 3D reconstruction technique.

As shown in FIG. 7, the ablation planning including:

501, selecting parameters and the application sequence of the ablation point on the GUI interface, the parameters of the ablation point include a size, a direction, a frequency and an overlapping rate of the ablation point;

502, obtaining a 3D model of the to-be-ablated tissue and an ablated area on the 3D model;

503, determining whether the ablation points of various parameters are traversed, and if so, ending, otherwise executing 504;

504, filling the ablation points on the 3D model according to the application sequence, and executing 503.

As shown in FIG. 2, FIG. 3, FIG. 4 and FIG. 5, filling the ablation points includes:

dividing the 3D model into a plurality of ablation layers in the direction perpendicular to the radio frequency direction of thermal ablation, and dividing the ablation layer into a plurality of strip-shaped first to-be-ablated blocks in the direction of radio frequency direction of thermal ablation. If an ablated area is in the first to-be-ablated blocks, dividing the first to-be-ablated block into a second to-be-ablated block and an ablated block, and the ablated block is located in front of the ablated area in the radio frequency direction of thermal ablation. Based on the estimated ablation length, sequentially placing and filling the ablation points of one parameter in the first to-be-ablated block and the second to-be-ablated block in the direction of the thermal ablation radio frequency.

Two adjacent ablation points are overlapped when the first to-be-ablated block and the second to-be-ablated block are filled with a plurality of ablation points, and a formula for calculating a thickness D of the ablation layer is:

$$D=d\times N$$

d is the diameter of the cylindrical ablation point, and N is the overlapping rate of the two adjacent ablation points.

Second Embodiment

An automatic planning device, on which an automatic planning method for tissue ablation corresponding to the first embodiment is applied, includes a memory and a processor, a computer program is stored in the memory, and the computer program is invoked by the processor to execute any method according to the first embodiment.

The first embodiment and the second embodiment provide an automatic planning method and a device for tissue ablation, the method includes 3D reconstructions technique and ablation planning, which can be safely and efficiently used for preoperative planning and intraoperative monitoring in the process of ultrasonic thermal ablation and postoperative evaluation, the ablation planning adopts primitive to depict the to-be-ablated tissue in the 2D image, and builds a 3D model of the to-be-ablated tissue in the 3D space, accepting the 3D input of the ablation area, when an unexpected event occurs and needs to be replanned, the 3D model and the ablated area can be updated to the new coordinate system, and the doctor does not need to manually mark the ablation point, which improves the accuracy and efficiency of ablation point planning.

In the description provided herein, numerous specific details are set forth. However, it is understood that embodiments of the disclosure may be practiced without these specific details. In some embodiments, well-known methods, structures and techniques have not been shown in detail in order not to obscure the understanding of this description.

It should be noted that, the above embodiments are only used to illustrate the technical solutions of the present disclosure, rather than limit the present disclosure thereto; although the present disclosure has been described in detail with reference to the above embodiments, for those skilled in the art, within the principles and spirit of the present disclosure it is still possible to modify the technical solutions described in the above embodiments, or to perform equivalent replacements for some or all of the technical features; and these modifications or replacements do not make the corresponding technical solutions deviate from the scope of the present disclosure.

What is claimed is:

1. An automatic planning device for tissue ablation, comprising:

a memory and a processor, wherein a computer program is stored in the memory, and the computer program is invoked by the processor to execute the following method:

obtaining a three dimensional (3D) model of a to-be-ablated tissue through a 3D reconstruction technique;

marking a cylindrical ablation point on the 3D model through an ablation planning, wherein an axial direction of the ablation point is the same as a radio frequency direction of thermal ablation; and displaying an ablated area on the 3D model;

wherein the 3D reconstruction technique comprises:
obtaining slice images of the to-be-ablated tissue in a plurality of directions, wherein the slice image in each direction comprises a plurality of two dimensional (2D) images;
depicting, by a primitive, the to-be-ablated tissue on the 2D images in one direction;
constructing the 3D model of the to-be-ablated tissue through the 3D reconstruction technique based the original 2D images; and displaying a cross section of the 3D model of the to-be-ablated tissue on the 2D image in other un-depicted directions;
wherein the ablation planning comprises:
selecting parameters of the ablation point and an implement sequence, wherein the parameters of the ablation point comprise a size, a direction, and a frequency of the ablation point;
filling the ablation point on the 3D model according to the implement sequence, wherein the filling comprises:
dividing the 3D model into a plurality of ablation layers in a direction perpendicular to the radio frequency direction of thermal ablation;
dividing the ablation layers into a plurality of strip-shaped first to-be-ablated blocks in the direction of radio frequency direction of thermal ablation;
in response that there is the ablated area in the first to-be-ablated block, dividing the first to-be-ablated block into a second to-be-ablated block and an ablated block, wherein the ablated block is located in front of the ablated area in the radio frequency direction of thermal ablation; and
filling the ablation points of one parameter in the first to-be-ablated block and the second to-be-ablated block;
wherein the parameters of the ablation point further comprise an overlapping rate, two adjacent ablation points are overlapped when a plurality of ablation points are provided between the first to-be-ablated block and the second to-be-ablated block.

2. The automatic planning device for tissue ablation according to claim 1, wherein a formula for calculating a thickness D of the ablation layer is:

$$D = d \times N$$

wherein d is a diameter of the cylindrical ablation point, and N is the overlapping rate of the two adjacent ablation points.

3. The automatic planning device for tissue ablation according to claim 1, wherein the method further comprises:
reobtaining a 2D image when the to-be-ablated tissue moves;
comparing a previous 2D image before moving and the reobtained 2D image which are in a same direction; and
transforming the 3D model and the ablated area on the 3D model together into a coordinate system of the reobtained 2D image.

4. The automatic planning device for tissue ablation according to claim 1, wherein the method further comprises:
implementing interpolation for the un-depicted 2D images based on the adjacent 2D image in the same direction.

5. The automatic planning device for tissue ablation according to claim 1, wherein the method further comprises:
setting a loss function before constructing the 3D model, and fine-tuning the primitive on the 2D image by the loss function, wherein a formula of the loss function Loss is:

$$Loss = 1 - (S_1 W_1 + S_2 W_2)$$

wherein $S_1$ is a similarity of a gray gradient and a gray mean value of edges of primitives on the two adjacent 2D images, $S_2$ is a similarity of primitives on the two adjacent 2D images, $W_1$ and $W_2$ are preset weights.

6. The automatic planning device for tissue ablation according to claim 5, wherein the fine-tuning comprises expansion, erosion and vertex offset.

7. The automatic planning device for tissue ablation according to claim 1, wherein the method further comprises:
implementing interpolation for tissues that are missing on the 2D image after depicting the 2D image of the to-be-ablated tissue.

8. The automatic planning device for tissue ablation according to claim 1, wherein the 3D reconstruction technique is an insight segmentation and registration toolkit (ITK) technique.

* * * * *